(12) United States Patent
Rice, Jr. et al.

(10) Patent No.: US 10,980,855 B2
(45) Date of Patent: Apr. 20, 2021

(54) TREATMENT OF DERMATOLOGICAL CONDITIONS

(71) Applicant: HYGIA BIOSCIENCE, Lowell, MA (US)

(72) Inventors: Kenneth L. Rice, Jr., Lowell, MA (US); Jennifer Bunce-Stone, Boxborough, MA (US)

(73) Assignee: HYGIA BIOSCIENCE, Lowell, MA (US)

( * ) Notice: Subject to any disclaimer, the term of this patent is extended or adjusted under 35 U.S.C. 154(b) by 0 days.

(21) Appl. No.: 16/945,078

(22) Filed: Jul. 31, 2020

(65) Prior Publication Data

US 2021/0030827 A1 Feb. 4, 2021

Related U.S. Application Data

(60) Provisional application No. 63/024,156, filed on May 13, 2020, provisional application No. 62/880,800, filed on Jul. 31, 2019.

(51) Int. Cl.
| | | |
|---|---|---|
| *A61K 36/54* | (2006.01) | |
| *A61K 31/745* | (2006.01) | |
| *A61K 9/00* | (2006.01) | |
| *A61P 17/02* | (2006.01) | |
| *A61K 35/06* | (2006.01) | |

(52) U.S. Cl.
CPC ............ *A61K 36/54* (2013.01); *A61K 9/0014* (2013.01); *A61K 31/745* (2013.01); *A61K 35/06* (2013.01); *A61P 17/02* (2018.01)

(58) Field of Classification Search
None
See application file for complete search history.

(56) References Cited

U.S. PATENT DOCUMENTS

| | | |
|---|---|---|
| 5,494,657 A | 2/1996 | Swenson |
| 9,248,160 B1 * | 2/2016 | Obagi .................... A61L 15/20 |
| 2009/0175927 A1 | 7/2009 | Gammelsaeter et al. |

OTHER PUBLICATIONS

International Search Report and Written Opinion received for PCT Application No. PCT/US2020/044546 dated Oct. 29, 2020, 7 pages.

* cited by examiner

*Primary Examiner* — Nannette Holloman
(74) *Attorney, Agent, or Firm* — Ann-Louise Kerner; Lathrop GPM LLP

(57) ABSTRACT

The present disclosure relates to an oxygen-permeable topically-applied composition (OPTC) and methods of its use for the treatment of skin conditions and injuries.

4 Claims, 2 Drawing Sheets

Before

After — OPTC

Before

After — Control

Fig. 2A
Fig. 2B
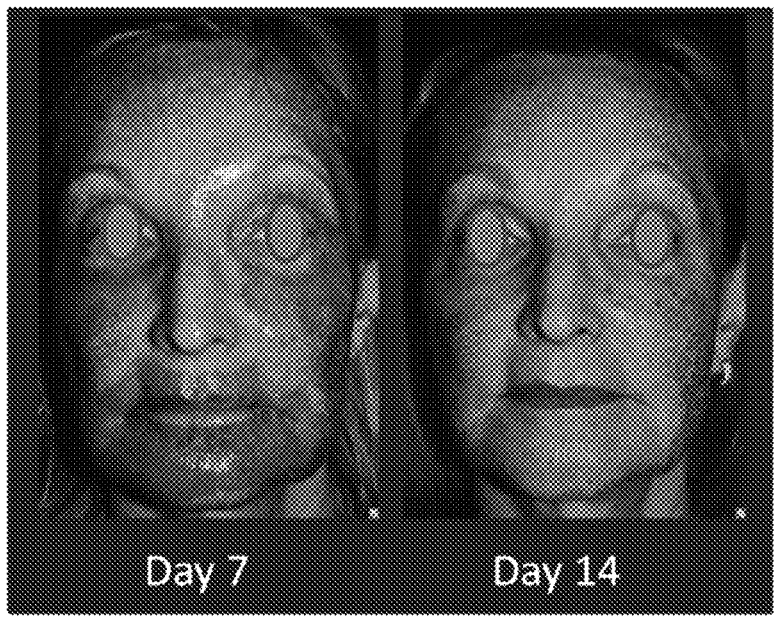
Day 7
Day 14
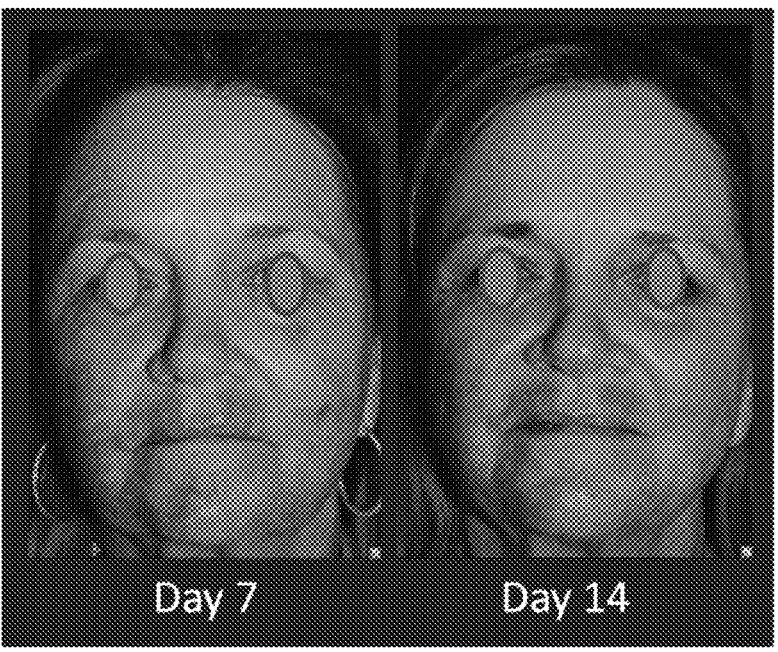
Day 7
Day 14
Fig. 2C
Fig. 2D

TREATMENT OF DERMATOLOGICAL CONDITIONS

CROSS-REFERENCE TO RELATED APPLICATIONS

This application claims the benefit under 35 U.S.C. § 119(e) of both U.S. Provisional Application No. 62/880,800, filed Jul. 31, 2019 and U.S. Provisional Application No. 63/024,156, filed May 13, 2020, each of which are also incorporated herein by reference in their entireties.

FIELD OF THE INVENTION

The present invention is in the field of medicine. More particularly, the invention relates to treatment of injured skin after laser ablation and/or scarring.

BACKGROUND OF THE INVENTION

Skin injuries and actinic lesions can result in scarring, edema, and/or erythema, the recovery from which can take months and even years, during which a subject suffering from such an injury can experience a lot of discomfort. Skin injuries can be the result of exposure to fire, caustic chemicals, ionizing irradiation. Skin lesions include keratosis, thickening and wrinkling, elastosis, telangiectasia, solar comedones, diffuse or mottled hyperpigmentation, acne scarring, and skin tears. Both can result in scarring, edema, and/or erythema.

Scarring, edema, and/or erythema can also be caused by procedures used to treat these injuries and lesions. Such treatment includes laser fractional ablation, used for example, to treat wrinkles (rhytids), discoloration, photodamage, tattoo removal, and acne scarring. Traditionally, the deeper the ablation, the more effective the treatment at improving the damage. However, with deeper ablation also comes edema and erythema, and potentially infection, leading to increased downtime with healing times often ten to fourteen days before skin re-epithelization. Ablating the skin necessarily disrupts the skin barrier, exposing the skin to infectious agents from the outside world. This elevates the risk of infection, the most common cause of scarring following treatment.[14] Thus, taking active preventative measures is critical following treatment.

The current treatment guideline to minimize this risk is the application of topical petroleum-based products to act as a barrier until the true skin barrier reforms.

Generally, formulations such as white petroleum or standard petrolatum ointment, are preferred to antibiotic ointments due to the propensity of the latter to cause contact dermatitis, particularly those containing neomycin. The hydrocarbon structure of petrolatum ointment makes it impermeability to oxygen. This structure aids in its barrier-like properties.

The basic concept of petroleum barriers is well justified. However, the standard petrolatum ointment contains emollients, additives and other ingredients such as lanolin, mineral oil, Panthenol, and glycerin that can cause localized reaction.[9, 10] Petrolatum ointment has been found to have a higher incidence of wound redness (52%) compared to those treated with pure white petrolatum (12%),[11] possibly due to irritation from these additives. In addition, the lack of oxygen permeability may result in longer healing times due to the increased metabolic demand of damaged tissue during healing that, accordingly, would benefit from exposure to oxygen to fuel the reparative process.

Thus, the lack of oxygen permeability, the thick consistency, and breadth of potential irritants in many petrolatum products when used can lead to unwanted side effects of unpleasant healing time and contact dermatitis and can result in longer healing times. Also. in a modern, busy society, post-operative downtime is a major factor for patients when considering aesthetic procedures.[2] As such, improving the recovery experience may result in more patients opting to do these procedures as well as higher subject satisfaction.

Thus, what is needed are improved formulations and methods for the treatment of skin injuries which facilitate and hasten healing, are non-irritating, effective in staving off infection, and which are easy to apply.

SUMMARY OF THE INVENTION

It has been discovered that oxygen-permeable topical formulations comprising petrolatum, avocado oil, and hydrogenated polyisobutene (Panalane), can take the place of lost natural sebum and can replicate its barrier and moisture retention functions. This discovery has been exploited to develop the present disclosure, which, in part, is directed to therapeutic formulations and methods for treating injured skin.

In one aspect, the present disclosure is directed to a protective, therapeutic nonaqueous, oxygen skin formulation which is a sebum replacement, oxygen-permeable, non-aqueous moisture barrier comprising 79.3% white petrolatum, 0.9% avocado oil, and 9.8% Panalane.

In another aspect, this formulation is used in a treatment for a patient that has undergone laser ablation of the skin, comprising topically administering to the ablated skin a therapeutically effective amount of the formulation such that re-epithelialization and reduction of edema and erythema of the ablated skin occurs.

In yet another aspect, the formulation is used in a method of treating a patient with a rash associated with incontinence dermatitis or diaper rash, the method comprising topically administering to the rash a therapeutically effective amount of a water-free, oxygen-permeable formulation, such that a reduction of rash, edema, and erythema of the ablated skin occurs.

DESCRIPTION OF THE DRAWINGS

The foregoing and other objects of the present disclosure, the various features thereof, as well as the disclosure itself may be more fully understood from the following description, when read together with the accompanying drawings in which:

FIGS. 2A-2D are photographic representations of two patients having undergone fractional ablative fractional $CO_2$ resurfacing, and then treatment with either OPTC or petrolatum ointment. The photographs show visual progression of healing between day 7 (left) and day 14 (right) following ablation. FIGS. 2A and 2B show the face of a patient during healing that had OPTC applied to the right side of her face control petrolatum ointment to the left side. FIGS. 2C and 2D show the face of a patient during healing that had OPTC applied to the left side of the face and control petrolatum ointment to the right side.

DESCRIPTION

Figure 1A:
FIGS. 1A-1D are representations of histograms of facial skin samples taken from different the sides of the face of a patient having undergone laser ablation and stained before being treated with OPTC (FIG. 1A) or before being treated with petrolatum ointment (FIG. 1C) and after treatment with OPTC (FIG. 1B) or with petrolatum ointment (FIG. 1D)

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

The present disclosure relates to an oxygen-permeable topically-applied composition (OPTC) or "formulations" and methods of its use for the treatment of skin conditions and injuries. When compared to the healing and protective capabilities of petrolatum-based ointments, OPTC formulations demonstrated significant oxygen-permeability while retaining the attractive barrier properties of petrolatum.

OPTC Formulation

The OPTC of the present disclosure is a topical formulation which provide barrier protection, maintain moisture, and facilitate healing while allow oxygen to reach the damaged tissue. This formulation comprises from about 75% to about 85% white petrolatum, from about 0.5% to about 1.2% avocado oil, and from about 15% to about 23% Panalane. In one example, the OPTC comprises about 79.3% white petrolatum, about 0.9% avocado oil, and about 19.8% Panalane. In another example, the OPTC consists essentially of 79.3% white petrolatum, 0.9% avocado oil, and 19.8% Panalane.

White petrolatum, CAS number 8009-03-8, is a semi-solid mixture of hydrocarbons with carbon numbers mainly higher than 25) and having a melting point is typically between 40° C. and 70° C. (105° F. and 160° F.). It is flammable only when heated to liquid. It is colorless or has a pale yellow color (when not highly distilled), translucent, and devoid of taste and smell when pure. It does not oxidize on exposure to the air and is not readily acted on by chemical reagents. It is insoluble in water. It is commercially available, e.g., from Unilever, Chicago, Ill.).

Panalane (H-300E or L-14E) is a hydrogenated polyisobutene that has moisturizing characteristics and aids in oxygen permeation through its nonocclusive hydrocarbon structure. It is commercially available, e.g., from Vantage, Specialty Chemicals, Chicago, Ill.).

Avocado oil is a plant-based oil that contains triglycerides, straight-chain saturated fatty acids (SFAs) and unsaturated fatty acids (UFAs). As components of natural lipid bilayers in the body, they act as effective water barriers as well to further preserve the skin's moisture without preventing the pass of oxygen. Avocado oil also includes further nourishing molecules such as β-sitosterol, β-carotene, lecithin, minerals, and vitamins A, C, D, and E. Avocado oil also has anti-inflammatory properties and helps to reduce erythema and swelling and re-epithelization. This oil comes as extra virgin, virgin, and pure, and is commercially available (e.g., from Chandiz Commercial Co., MirAmerica Inc., Manqueley).

The OPTC does not contain any water, alcohol, emulsifiers, emollient extenders, preservatives, or artificial colorings, resulting in a hypoallergenic product that mitigates the risk of contact dermatitis. In some forms it also may not contain any anti-bacterial agents.

The OPTC can be prepared as follows using a 55-gallon batch as an example. One or more electric barrel warmers are attached to a 55-gallon drum of white petrolatum which is heated until the contents are completely liquified. Using a clean pump, about 11 gallons of the liquified petrolatum are removed and transferred to another container for future use. About 11 gallons of Panalane in its liquid form are added to the remaining petrolatum along with 55 ounces of avocado oil. Using a stainless-steel paddle, the mixture is stirred to consistency. The mixture is then heated to about 135 to degrees F. to about 140 degrees F. for about one hour. The mixture is then transferred to a filling apparatus to fill smaller containers (e.g., tubes or jars) as needed.

Conditions to be Treated

The composition according to the disclosure can be used to treat many conditions and lesions affecting the epidermis and dermis. For example, incontinence dermatitis or chronic inflamed rash from incontinence episodes can be treated with OPTC. These rashes are often suffered by adults living in nursing or convalescent homes, and which require on-going prophylaxis. In another example, pediatric diaper rash suffered at least once and often repeated in children under 3 can be treated with OPTC. Diaper rash in children under the age of three is a painful irritation in the buttocks and genital area caused by the constant contact with moist or wet diapers containing irritating waste products. In both of these conditions, once the rash is resolved, OPTC can be used as a prophylactic treatment.

Other nonlimiting examples of conditions that can be treated with OPTC include dermal scars, radiation- and chemically-damaged skin, post-operative surgical or ablative procedure side effects such as such as erythema and swelling, moisture loss and skin damaged by laser or surgical procedures, atopic dermatitis (eczema), cosmetic surgery aftercare, dry, chapped skin, insect bites, minor abrasions and lacerations, minor burns, pressure ulcers, radiation dermatitis, skin tears, and xerotic eczema.

Methods of Treatment

The target area is washed with water, mild soap, or any wound cleansing solution as directed by a physician and patted dry. The lesion is treated topically by applying the OPTC formulation directly from the tube or by removing the desired amount with a scoop, spatula, finger, or other device. Application can be achieved by fingertip or using an applicator as directed by a physician and then gently messaged the formulation onto the target area.

Approximately 2.5 cm formulation from a tube is applied per inch of target area. The formulation can be warmed on the hand before application. The formulation is applied at least once a day, and from about three times a day to about 12 times a day for one day to about 30 days, depending on the condition of the lesion to be treated.

Initial dermatological trauma and healing can be followed by visual inspection of the area. In addition, samples can be taken from the treated lesion and observed microscopically after staining with any known dermatological stain, e.g., hematoxylin and eosin (H&E) which is a standard tissue section staining method based on binding of nucleic acid and other acidic components of the tissue to the basic hematoxylin stain, and wherein the acidic counter stain, eosin, binds to basic components in the tissue, such as cytoplasmic proteins. Another useful staining method is the Mason Trichrome (MT) method often used in wound healing studies. Additionally, the Periodic acid—Schiff (PAS) staining method can be used for staining of polysaccharides such as glycogen, and muco-substances such as glycoproteins, glycolipids and mucins in tissues, and the Toluidine blue statin method can be used for staining of mast cells that are found in the connective tissue and their cytoplasm contains granules composed of heparin and histamine.

Quantitative studies show that OPTC promotes 75% re-epithelialization of radiation-damaged skin in as little as 72 hours, is better at reducing inflammation, leaves virtually no residuals on the skin, and offers a 20% increase in initial and residual barrier properties over a commonly-used petrolatum-based t competitive product.

Reference will now be made to specific examples illustrating the disclosure. It is to be understood that the examples are provided to illustrate exemplary embodiments and that no limitation to the scope of the disclosure is intended thereby.

EXAMPLES

Example 1

Treatment after Ablative Fractional Resurfacing

Subject Population:
Twenty subjects exhibiting moderate photodamage (Glogau scale 3) were randomized into this prospective IRB-approved study. Written informed consent was obtained from each patient. Exclusion criteria were pregnancy, breast-feeding, and use of oral retinoids six months prior to treatment, active infection, or lesions suspicious for malignancy. The first 20 subjects to meet inclusion criteria were enrolled in the study and all 20 completed the trial in its entirety.
Study Design:
This was a prospective, single-arm, split-face, double-blind, controlled, pilot study conducted to study the effect of immediate application of topical OPTC on post-operative wound healing following fractional ablative laser resurfacing versus control.

In a split-face model, prior to the procedure, each subject received a topical anesthetic gel containing 20% benzocaine, 8% lidocaine, and 4% tetracaine. Each subject received one full face treatment with a fractional ablative carbon dioxide laser (Lumenis Ultra Pulse ActiveFX Santa Clara, Calif.) or fractional ablative erbium:YAG laser (Joule™ ProFractional™, Sciton, Inc., Palo Alto, Calif.). Settings were individually determined based on the subject skin type and degree of photodamage.

Figure 1B:
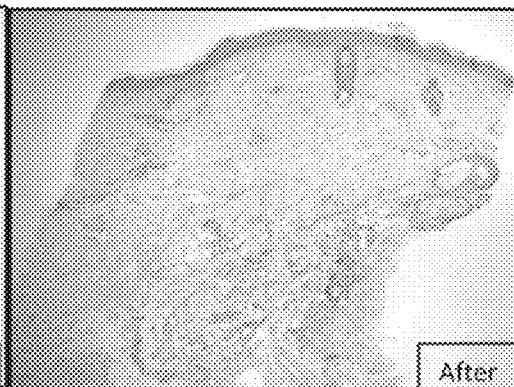
Figure 1C:
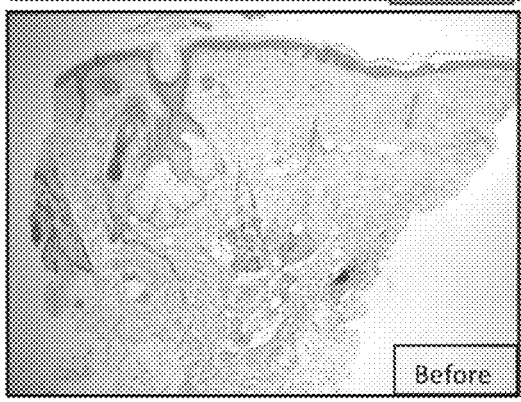
Figure 1D:
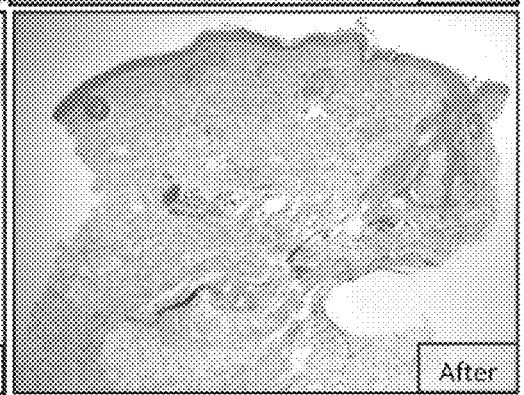

Following laser treatment, subjects were given a seven-day post-operative skin care regimen consisting of daily application of topical OPTC on one side of face and control petrolatum ointment on the other. The sides of the face receiving OPTC and control were randomized by coin toss prior to the procedure and blind to both the patient and treating physician.
Clinical Assessment:
To assess post-operative wound healing, three blinded investigators evaluated photographs taken at baseline, Day 7, Day 14, and Day 30 following laser treatment. Photographs were obtained using identical camera settings, lighting conditions, and patient positioning (Nikon D300, 13.1 million total pixels, 12.3 million effective pixels). Evaluation criteria included the number of days until re-epithelialization and the level of edema and erythema. The latter were assessed individually using a quartile scale: 0 (no edema/erythema); 1 (mild edema/erythema); 2 (moderate edema/erythema); and 3 (severe erythema or edema).
Histological Assessment
Histology was performed on 8 3 mm biopsies taken from both side of the face of subjects before and after laser treatment. The samples were stained with Hematoxylin and Eosin. This is a classic standard tissue section staining method widely used for the inspection of tissue components for pathological analysis that's applicable in all organs and disease models.
Photographic Assessment
Photograms of patient faces were taken before and after treatment at days 7 and 14.
Results:
All 20 subjects completed the trial fully per the protocol. The histograms (FIG. 1) showed a degree of primarily perifollicular lymphocytic inflammation in the initial biopsies. This inflammatory component diminished between the original and subsequent biopsies in both treatment groups. No significant differences were observed between the biopsies taken from the two sides of the face of each patient.

At all evaluated intervals, subjects showed no statistically significant differences in time to re-epithelialization ($p=1$), erythema ($p=0.9$ at day 7, $p=0.7$ at day 14) or edema ($p=0.9$ at day 7, $p=0.5$ at day 14) compared to Petrolatum ointment. All patients re-epithelialized by day 7.

At day 7, 17 patients (85%) indicated that they had a treatment preference in treatment product. Sixteen patients (94% of those with a preference, 80% of total sample) stated they preferred the OPTC based on the criteria of skin feel and ease of use and 1 patient (5% of total sample) that they preferred the petrolatum ointment. By day 14, all 17 of patients (85% total sample) indicated a preference for OPTC.

Thus, oxygen-permeable topical creams such as OPTC are a safe and effective alternative to standard petrolatum ointment for use in post-operative healing following laser resurfacing. It provides at minimum at least equivalent barrier qualities that generated petrolatum ointment's widespread usage without any potential irritants to sensitive skin, and speeds up re-epithelialization. The overwhelming patient preference for the OPTC adds to its status as a viable alternative in wound healing to optimize healing time and increase patient satisfaction.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A method of treating a patient that has undergone laser ablation of the skin, comprising topically administering to an ablated skin of the patient a therapeutically effective amount of a water-free, oxygen-permeable formulation such that re-epithelialization and reduction of edema and erythema of the ablated skin occurs, the formulation comprising: white petrolatum; avocado oil; and [Panalane] hydrogenated polyisobutene.

2. The method of claim 1, wherein the formulation comprises 79.3% white petrolatum, 0.9% avocado oil, and 19.8% [Panalane] hydrogenated polyisobutene.

3. A method of treating a patient with a rash associated with incontinence dermatitis or diaper rash, the method comprising topically administering to the rash a therapeutically effective amount of a water-free, oxygen-permeable formulation, such that a reduction of rash, edema, and erythema of the ablated skin occurs, the formulation comprising: white petrolatum; avocado oil; and [Panalane] hydrogenated polyisobutene.

4. The method of claim 3, wherein the formulation comprises 79.3% white petrolatum, 0.9% avocado oil, and 19.8% [Panalane] hydrogenated polyisobutene.

\* \* \* \* \*